United States Patent [19]

Imamura et al.

[11] 4,399,289
[45] Aug. 16, 1983

[54] 2-DIPHENYLMETHYLENEAMINO-3-INDOLYLPROPIONITRILE AND ALKYL ESTERS OF 2-DIPHENYLMETHYLENE-AMINO-3-INDOLYLPROPIONIC ACID

[75] Inventors: Shinzo Imamura; Haruyo Sato; Hiroyoshi Kuramoto, all of Nagoya, Japan

[73] Assignee: Toray Industries, Inc., Tokyo, Japan

[21] Appl. No.: 247,938

[22] Filed: Mar. 26, 1981

[30] Foreign Application Priority Data

Mar. 31, 1980 [JP] Japan ............................ 55-40470
Jan. 26, 1981 [JP] Japan ............................ 56-8998

[51] Int. Cl.³ .................. C07D 209/18; C07D 209/20
[52] U.S. Cl. ................................ 548/507; 548/496; 548/505
[58] Field of Search ................ 260/326.15; 548/495, 548/505, 507

Primary Examiner—Donald G. Daus
Assistant Examiner—D. B. Springer
Attorney, Agent, or Firm—Austin R. Miller

[57] ABSTRACT

Novel indole derivatives of the general formula I can be obtained by reacting, directly or indirectly, N,N-dimethyl-3-indolemethylamine with a Schiff base of the general formula II,

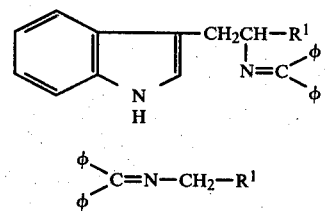

in which $R^1$ is cyano or methoxycarbonyl, ethoxycarbonyl, propoxycarbonyl or butoxycarbonyl, and $\phi$ is phenyl. The successive hydrolysis of the indole derivatives of the general formula I in the presence of an acid and of a base gives tryptophane.

2 Claims, No Drawings

2-DIPHENYLMETHYLENEAMINO-3-INDOLYL-PROPIONITRILE AND ALKYL ESTERS OF 2-DIPHENYLMETHYLENE-AMINO-3-INDOLYL-PROPIONIC ACID

BACKGROUND OF THE INVENTION

The invention relates to novel indole derivatives and a process for the preparation thereof.

Tryptophane is one of the essential amino acids and is widely utilized as medicine and food or feed additives.

There is known a process for the synthesis of tryptophane by reacting an α-isocyanoacetic acid ester with a quaternary salt of N,N-dimethylindolemethylamine (hereinbelow, referred to as gramine) to obtain an α-isocyano-β-(3-indole)propionic acid derivative, and then hydrolyzing the derivative (see, Japanese Laid-open Patent Application No. 48-26758). This process is partly satisfactory but leaves the following points to be improved.

A. Many steps are required to obtain an α-isocyanoacetic acid ester from the starting material. In general, many steps are required to synthesize amino acids from simple starting materials. However, the commercial synthesis of amino acids should be attained by reduced steps. From this point of view, the above-mentioned process necessitates too many steps.

B. The above-mentioned α-isocyanoacetic acid ester is chemically unstable owing to the isocyano group and, therefore, the above-mentioned process which employs the ester as a starting material may often cause undesirable side reactions, which may cause a reduction in the yield. The process has a low processability and emits a foul odor.

C. By-products which are formed in the course of the conversion of the above-mentioned derivatives to amino acids cannot be reused. From the viewpoint of saving natural resources, it is desirable to be able to recycle the by-products to the process for the reuse thereof.

Therefore, it has been earnestly desired to develop a process for synthesizing tryptophane, in which only a few steps are required, the intermediate before the hydrolysis should be stable and a high yield should be obtainable and the by-products should be reusable.

BRIEF SUMMARY OF THE INVENTION

It is an object of the present invention to provide chemically stable intermediates usable for the synthesis of tryptophane.

Another object of the present invention is to provide a process for preparing such intermediates, which process contains a few steps and is capable of producing the product in a high yield.

A further object of the present invention is to provide a process for preparing such intermediates, the by-products of which, produced by the synthesis of tryptophane from the intermediates, can be reused.

Thus, the present invention provides indole derivatives of the following general formula I,

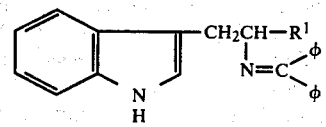

in which $R^1$ is cyano or methoxycarbonyl, ethoxycarbonyl, propoxycarbonyl or butoxycarbonyl, and $\phi$ is phenyl.

The present invention also provides a process for preparing the indole derivatives of formula I, which comprises reacting an N-(alkyl)-N,N-dimethyl-3-indolemethylammonium salt or N-(benzyl)-N,N-dimethyl-3-indolemethylammonium salt of the general formula IV,

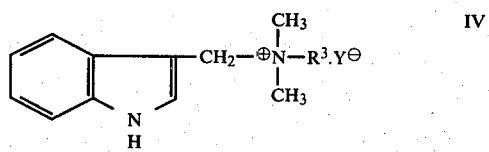

in which $R^3$ is methyl, ethyl, propyl, butyl or benzyl, and $Y^\ominus$ is a hydrogensulfate, alkylsulfate, chloride, bromide or iodide anion, with a Schiff base of the general formula II,

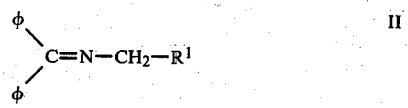

in which $R^1$ and $\phi$ are as defined above, in a monophase or two-phase solvent system, in the presence of a base, with or without the use of a catalyst, at a temperature of from 0° to 80° C.

The indole derivatives of formula I may also be prepared by reacting gramine with a Schiff base of the general formula II,

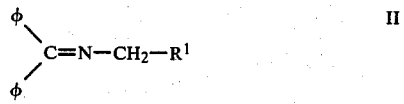

in which $R^1$ and $\phi$ are as defined above, in a monophase or two-phase solvent system, in the presence of at least one alkylating agent selected from the group consisting of halogenated hydrocarbons of the general formula III,

in which $R^2$ is methyl, ethyl, propyl, butyl or benzyl and X is a chlorine, bromine or iodine atom, and dimethyl sulfate and in the presence of a base, with or without the use of a catalyst, at a temperature of from 0° to 80° C.

DETAILED DESCRIPTION OF THE INVENTION

Hereinbelow, the processes of the present invention will be first described and, then, the novel compounds prepared by the process will be described.

The present invention includes two processes, one of which is a direct process and the other is an indirect process. In the indirect process, gramine is first converted to an N-(alkyl)-N,N-dimethyl-3-indolemethylammonium salt or N-(benzyl)-N,N-dimethyl-3-indolemethylammonium salt (hereinbelow, referred to as gramine quaternary salt) and this gramine quaternary salt is reacted with a Schiff base as mentioned below. On the other hand, in the direct process, gramine is reacted with the Schiff base and with an alkylating agent as described below. These reactions may be represented by the following reaction formula:

Indirect Process:

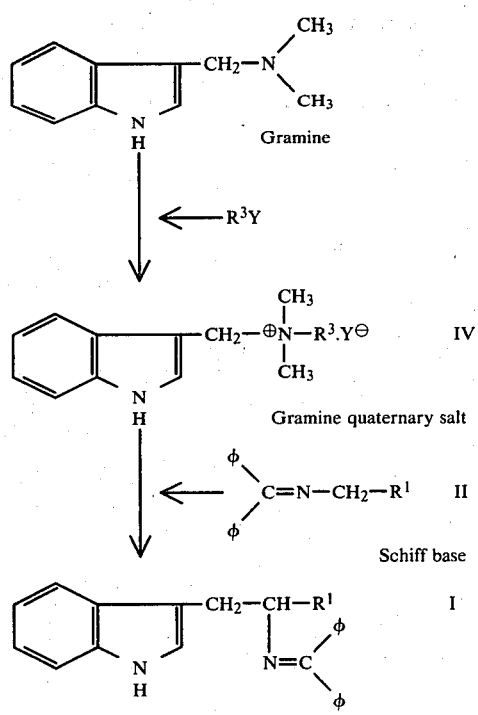

Direct Process:

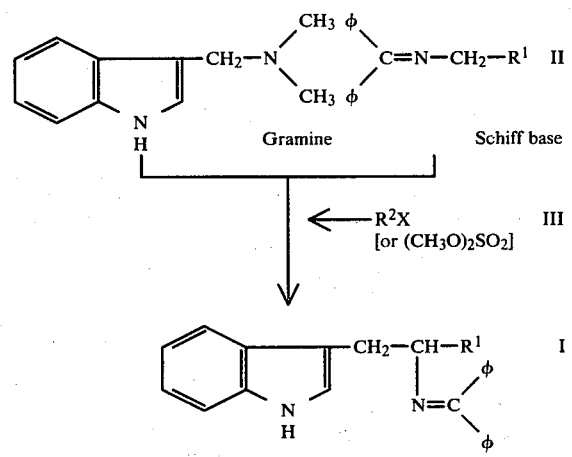

in which formulae, $R^1$ and $\phi$ are as defined above, $R^2$ is methyl, ethyl, propyl, butyl or benzyl, and X is a chlorine, bromine or iodine atom.

Gramine may be obtained quantitatively by reacting indole with dimethylamine and formaldehyde [Ber., 68, 436 (1936)].

The gramine quaternary salts may be obtained by reacting gramine with at least one alkylating agent selected from alkyl halides and dimethyl sulfate. For example, by reacting gramine with methyl iodide, N,N,N-trimethyl-3-indolemethylammonium iodide can be obtained in a high yield [J. Am. Chem. Soc., 66, 220 (1944)]. If gramine is reacted with dimethyl sulfate, N,N,N-trimethyl-3-indolemethylammonium methylsulfate can be obtained [Monatsh, 88, 768 (1958)]. The alkyl halides include methyl iodide, methyl bromide, ethyl iodide, ethyl bromide, propyl iodide, propyl bromide, butyl iodide, benzyl chloride, benzyl bromide and the like.

The Schiff bases of formula II usable for the present invention may be prepared by two processes.

One is a process wherein a glycine ester obtained by reacting glycine with an alcohol of 1 to 4 carbon atoms is subjected to a dehydration reaction with benzophenone [Tetrahedron Lett., No. 30, 2641 (1978)]. The other is a process wherein aminoacetonitrile is reacted with benzophenone [Tetrahedron Lett., No. 30, 4625 (1978)]. N-(diphenylmethylene)glycine alkyl esters are obtained by the former process and N-(diphenylmethylene)aminoacetonitrile is obtained by the latter process. As the alkyl N-(diphenylmethylene)glycinate, there may be mentioned methyl N-(diphenylmethylene)glycinate, ethyl N-(diphenylmethylene)glycinate, propyl N-(diphenylmethylene)glycinate and butyl N-(diphenylmethylene)glycinate.

Examples of the gramine quaternary salts usable for the present invention are N,N,N-trimethyl-3-indolemethylammonium hydrogensulfate, N,N-dimethyl-N-propyl-3-indolemethylammonium hydrogensulfate, N,N,N-trimethyl-3-indolemethylammonium methylsulfate, N,N-dimethyl-N-ethyl-3-indolemethylammonium methylsulfate, N-benzyl-N,N-dimethyl-3-indolemethylammonium chloride, N,N-dimethyl-N-ethyl-3-indolemethylammonium bromide, N-butyl-N,N-dimethyl-3-indolemethylammonium bromide, N,N,N-trimethyl-3-indolemethylammonium iodide and N,N-dimethyl-N-ethyl-3-indolemethylammonium iodide.

The gramine quaternary salts and Schiff bases thus obtained are reacted together. The reaction may be effected by two processes. One is a process wherein the reaction is effected in a homogeneous solvent, i.e. a monophase solvent system, the other is a process wherein the reaction is effected in a two-phase solvent system consisting of an aqueous phase and an organic phase. It is desirable that the reaction is effected by the latter process, since the base should preferably be employed as an aqueous solution and the reaction should preferably be carried out under a mild condition.

The reaction is carried out in the solvent, in the presence of a base, with or without the use of a catalyst, and at a temperature of from 0° to 80° C. In the case where $Y^\ominus$ of the employed gramine quaternary salt is a hydrogensulfate anion or an alkylsulfate anion, it is not necessary to use a catalyst. Thus, in the case where $Y^\ominus$ is a chloride, bromide or iodide anion, a catalyst should be used. As the catalyst, there may be employed halides, hydrogensulfates or hydroxides of tetraalkylammoniums or benzyltrialkylammoniums, having 1 to 6 carbon atoms in each alkyl group, preferably quaternary ammonium salts such as tetrabutylammonium hydrogensulfate, benzyltrimethylammonium chloride, benzyltrimethylammonium hydroxide, cetyltrimethylammonium bromide, dodecyltrimethylammonium chloride and tetraethylammonium hydroxide, more preferably tetrabutylammonium hydrogensulfate, benzyltrimethylammonium hydroxide and tetraethylammonium hydroxide. The catalyst may be employed in an amount of from 0.001 to 2 equivalents, preferably 0.01 to 1 equivalent, based on the gramine quaternary salt. If the catalyst is employed in an amount less than 0.001 equivalents, both the yield of the final product and the reaction rate are low. If the amount of the catalyst is larger than 2 equivalents, it is difficult to isolate the final product from the reaction mixture.

The reaction temperature should be from 0° to 80° C., preferably 0° to 40° C. Where the temperature is too low, the reaction proceeds too slowly. When the temperature is too high, side reactions may undesirably occur and, further, in the case of the reaction in the two-phase solvent system, hydrolysis may undesirably occur.

The base may be employed in an amount of from 0.5 to 20 equivalents, preferably 1 to 10 equivalents, based on the gramine quaternary salt.

In the case of the reaction in the monophase solvent system, there may be employed, as the solvent, aliphatic alcohols such as methanol, ethanol, propanol and butanol, halogenated hydrocarbons such as dichloromethane, chloroform, trichloroethylene and trichloroethane, aromatic hydrocarbons such as benzene, toluene and xylene, ethers such as diethyl ether, tetrahydrofuran and dioxane, dimethylformamide, and dimethyl sulfoxide. When these solvents are employed in the reaction system, it is preferable to employ a base selected from alkali metals and the hydrides and alkoxides thereof.

In the case of the reaction in the two-phase solvent system, there may be employed a mixture of water with at least one organic solvent selected from the above-mentioned halogenated hydrocarbons, ethers, aromatic hydrocarbons, dimethylformamide and dimethyl sulfoxide. In such a case, there may preferably be employed, as the base, hydroxides, carbonates and hydrogencarbonates of alkali metals such as sodium hydroxide, sodium carbonate and sodium hydrogen carbonate. However, where an alkali metal hydroxide is used, chloroform and trichloroethylene should not be employed in the solvent since explosive compounds, such as carbene and dichloroacetylene, may probably be formed in the system.

In both the above-mentioned reactions, the starting materials may be employed in an approximately stoichiometric amount, preferably 0.8 to 1.0 mol equivalent of the gramine quaternary salt should be employed based on the Schiff base.

The reaction may be carried out under atmospheric pressure or under increased or reduced pressure, preferably under atmospheric pressure. The reaction may be effected batch-wise, continuously or semi-continuously. In the case of the batch-wise reaction, the reaction may usually be completed in from 1 to 3 hours.

Where the reaction is effected batch-wise, it is preferably that the gramine quaternary salt is added to a mixture of the Schiff base, the base, the solvent and the catalyst (if any) with stirring.

After the completion of the reaction, the product of formula I, as hereinbefore defined, may be isolated in a usual way. For example, where the two-phase solvent system is employed, the solvent is removed from the organic phase which is separated from the aqueous phase after the completion of the reaction, and the residue is passed through a column packed with silica gel. As the developing solvent, cyclohexane or a cyclohexane-ethyl acetate may suitably be used. After the removal of the solvent from the eluate under reduced pressure, a pure indole derivative is obtained.

In the case where the desired compound is isolated from the reaction mixture obtained in the monophase solvent system, since there exists in the reaction mixture a compound which should not be brought into contact with water, such as sodium, potassium or sodium alkoxide, such a compound should first be decomposed carefully with a little water. The organic phase is concentrated, and then the product is isolated as mentioned above in a similar manner as in the two phase solvent system.

The direct process will now be explained in detail below. As the halogenated hydrocarbons employed in this process as the alkylating agent, there may be mentioned methyl iodide, methyl bromide, ethyl iodide, ethyl bromide, propyl bromide, propyl iodide, butyl bromide, butyl iodide, benzyl chloride, benzyl bromide and the like.

In the case where the halogenated hydrocarbons are employed as the alkylating agent, it is preferable to also employ a catalyst in the reaction system. In the case where dimethyl sulfate is employed as the alkylating agent, the reaction proceeds well in the absence of a catalyst.

As a catalyst, there may be employed those mentioned hereinbefore with respect to the indirect process. The catalyst may be employed in an amount of from 0.0001 to 2 equivalents, preferably 0.01 to 1 equivalent, based on the employed halogenated hydrocarbon, but not on the gramine quaternary salt as in the indirect process.

The reaction temperature should again be from 0° to 80° C., preferably 0° to 40° C., and the base may be employed in an amount of from 0.5 to 20 equivalents, preferably 1 to 10 equivalents, based on the alkylating agent.

The upper and lower limits of these values have the same meanings as those in the indirect process.

In the direct process, the reaction may be effected in a monophase solvent system or in a two-phase solvent system, and in both cases, the same kinds of solvent and base as in the indirect process may be employed. Thus, it will be appreciated that, also in the direct process, chloroform and trichloroethylene should not be used together with the alkali metal hydroxides.

As a rule, gramine and a Schiff base should be reacted in an approximately stoichiometric amount. However, it is preferable to employ 0.8 to 1.0 mol equivalent of gramine based on the Schiff base.

The alkylating agent may be employed in an amount of from 1 to 3 mol, preferably 1 to 1.5 mol, based on the Schiff base.

The pressure, system and time of the reaction may be the same as those in the indirect process.

Where the reaction is effected batch-wise, it may be suitable that the alkylating agent is added to the mixture of the Schiff base, gramine, base, solvent and catalyst (if any) with stirring.

The final product may be isolated and purified as mentioned above with respect to the indirect process.

According to the processes of the present invention as explained above, the following specific effects can be attained:

Desired products can be obtained in a high yield.

These processes can generally be carried out under a mild condition and, thus, are industrially advantageous.

These processes can be carried out by a simple apparatus and operation.

The Schiff bases to be used as a starting material in the present process are stable in an aqueous alkali solution and can be purified by distillation or crystallization.

The novel compounds of general formula I, as obtained as mentioned above, include 2-diphenylmethyleneamino-3-indolepropiononitrile, methyl 2-diphenylmethyleneamino-3-indoleproprionate, ethyl 2-diphenylmethyleneamino-3-indolepropionate, propyl 2-diphenylmethyleneamino-3-indolepropionate, and butyl 2-diphenylmethyleneamino-3-indolepropionate.

The novel compounds of the present invention can easily be converted to tryptophane by successive hydrolysis in the presence of an acid and then of a base or in the presence of a base and then of an acid.

During the hydrolysis of the compounds of formula I, benzophenone is formed by as a by-product. The benzophenone may be recycled and reused as a starting material for the production of the Schiff bases usable for the present invention. This is one of the specific features of the present invention.

Furthermore, in the case where the above-mentioned hydrolysis is carried out subsequent to the processes of the present invention, it is not necessary to isolate the final compound of formula I from the reaction mixture and purify it. This is another specific feature of the present invention.

The present invention will further be illustrated by the following non-limitative examples.

EXAMPLE 1

A 50 ml Erlenmeyer flask equipped with a magnetic stirring bar was charged with 2.2 g (0.01 mol) of N-(diphenylmethylene)aminoacetonitrile, 3.0 g (0.01 mol) of N,N,N-trimethyl-3-indolemethylammonium methysulfate, 20 ml of dichloromethane and 2.0 g (0.05 mol) of sodium hydroxide in 3.7 g of water (35% aqueous solution). The mixture was stirred for 3 hours at room temperature. Stirring was stopped. The organic phase was washed with water, dried over anhydrous magnesium sulfate, and evaporated under reduced pressure with a rotary evaporator. The pale yellow residue was placed on a silica gel column and was eluated with 1:4 (V/V) ethyl acetate-cyclohexane. Fractions containing the product were combined and evaporated, affording 3.11 g (89.1%) of 2-diphenylmethyleneamino-3-indolepropionitrile as pale yellow oil. The analytical values of this compound are given in Table 1.

EXAMPLE 2

A 100 ml Erlenmeyer flask equipped with a magnetic stirring bar was charged with 5.3 g (0.020 mol) of ethyl N-(diphenylmethylene)glycinate 6.0 g (0.020 mol) of N,N,N-trimethyl-3-indolemethylammonium methylsulfate, 50 ml of dichlormethane and 3.7 g (0.060 mol) of sodium hydroxide in 4.5 g of water (35% aqueous solution). The mixture was stirred for 3 hours at room temperature. Stirring was stopped. The organic phase was washed with water, dried over anhydrous magnesium sulfate, and evaporated under reduced pressure with a rotary evaporator. The pale yellow residue was placed on a silica gel column and was eluated with 1:4 (V/V) ethyl acetate-cyclohexane. Fractions containing the product were combined and evaporated, affording 7.6 g (95.8%) of ethyl 2-diphenylmethyleneamino-3-indolepropionate. The analytical values of this compound are given in Table 1.

EXAMPLE 3~EXAMPLE 5

Methyl 2-diphenylmethyleneamino-3-indolepropionate, propyl 2-diphenylmethyleneamino-3-indolepropionate, and butyl 2-diphenylmethyleneamino-3-indolepropionate were prepared in a manner similar to that in Example 2. The analytical values of these compounds are given in Table 1.

EXAMPLE 6

This example illustrates the following reaction:

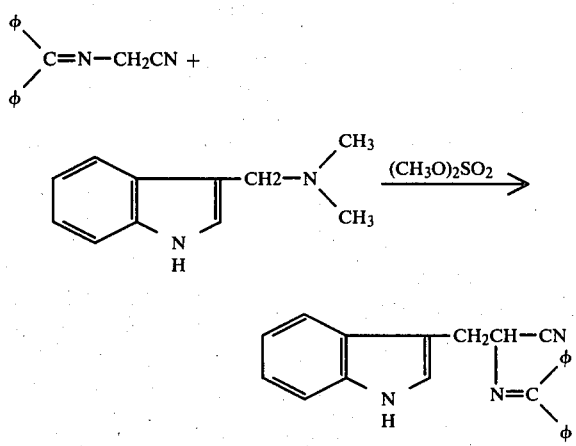

A 100 ml Erlenmeyer flask equipped with a magnetic stirring bar and a dropping funnel was charged with 2.2 g (0.01 mol) of N-(diphenylmethylene)aminoacetonitrile, 1.74 g (0.01 mol) of gramine, 60 ml of dichloromethane, and 2.0 g (0.05 mol) of sodium hydroxide in 3.7 g of water (35% aqueous solution). In the dropping funnel were placed 1.9 g (0.015 mol) of dimethyl sulfate and 10 ml of dichloromethane. The contents of the flask were stirred at room temperature as the dimethyl sulfate solution was added over 1 hour. The reaction mixture was stirred for additional 7 hours. Stirring was stopped. The organic phase was washed with water, dried over anhydrous magnesium sulfate, and evaporated under reduced pressure with a rotary evaporator. The pale yellow residue was placed on a silica gel column and was eluated with 1:4 (V/V) ethyl acetate-cyclohexane. Fractions containing the product were combined and evaporated, affording 3.12 g of 2-diphenylmethyleneamino-3-indolepropiononitrile. The yield is shown in Table 2.

EXAMPLE 7~EXAMPLE 9

2-Diphenylmetheneamino-3-indolepropionitrile was prepared by reaction of N-(diphenylmethylene)aminoacetonitrile with gramine, by addition of an alkyl halide instead of dimethyl sulfate in a manner similar to that in Example 6 (Table 2).

TABLE 2

| Example No. | Alkylating Agent | Yield (%) |
|---|---|---|
| 6 | (CH$_3$O)$_2$SO$_2$ | 89.4 |
| 7 | CH$_3$I | 84.8 |
| 8 | C$_4$H$_9$Br | 81.3 |
| 9 | ⟨phenyl⟩—CH$_2$Cl | 86.1 |

EXAMPLE 10

A 100 ml Erlenmeyer flask equipped with a magnetic stirring bar and a dropping funnel was charged with 2.67 g (0.01 mole) of ethyl N-(diphenylmethylene)glycinate, 1.74 g (0.01 mole) of gramine, 60 ml of dichloromethane, and 4.0 g (0.01 mol) of sodium hydroxide in 7.5 g of water (35% aqueous solution). In the dropping funnel were placed 1.9 g (0.015 mol) of dimethyl sulfate and 10 ml of dichloromethane. The contents of the flask were stirred at room temperature as the dimethyl sulfate solution was added over 1 hour. The reaction mixture was stirred for another 1 hour. Stirring was stopped. The organic phase was washed with water, dried over anhydrous magnesium sulfate and evaporated under reduced pressure. The residue was placed on a silica gel column and eluated with 1:4 (V/V) ethyl acetate-cyclohexane. Fractions containing the product were combined and evaporated, affording 3.4 g (85.8%) of ethyl 2-diphenylmethyleneamino-3-indolepropionate.

EXAMPLE 11~EXAMPLE 13

Ethyl 2-diphenylmethyleneamino-3-indolepropionate was prepared by reaction of ethyl N-(diphenylmethylene)glycinate with gramine, by addition of alkyl halide instead of dimethyl sulfate in a manner similar to that in Example 10 (Table 3):

TABLE 3

| Example No. | Alkyl Halide | Yield (%) |
|---|---|---|
| 11 | CH₃I | 84.4 |
| 12 | C₂H₅Br | 81.2 |
| 13 | 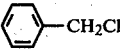 | 87.5 |

EXAMPLE 14

A 500 ml flask is equipped with a mechanical stirrer and a dropping funnel. The flask was charged with 25.3 g (0.1 mol) of methyl N-(diphenylmethylene)glycinate, 17.4 g (0.1 mol) of gramine, 300 ml of dichloromethane, and 28.1 g (0.5 mol) of potassium hydroxide in 52.1 g of water (35% aqueous solution). The contents of the flask were stirred at room temperature as a solution of 18.9 g (0.15 mol) of dimethyl sulfate in 50 ml of dichloromethane was added over 1 hour. The mixture was stirred for another 1 hour and then the organic phase was separated.

A solution of 15 g of concentrated hydrochloric acid in 15 ml of ethanol was added to the organic phase and the mixture was stirred for 1 hour at room temperature. After 50 ml of water were added, the mixture was stirred for an additional 15 minutes. After the water phase was separated, the organic phase was extracted with two 50 ml portions of water. To the combined aqueous extracts 50 ml of concentrated aqueous ammonia and 50 g of ammonium chloride were added. The mixture was then extracted with two 100 ml portions of dichloromethane. The organic extracts were dried over anhydrous magnesium sulfate, and evaporated, affording 18.3 g (83.6%) of crude tryptophane methyl ester.

EXAMPLE 15

To combined aqueous extracts obtained using the same procedure as Example 14, 16 g of sodium hydroxide were added and the mixture was stirred for 1 hour. The resulting aqueous solution was passed through strong cation-exchange resin (PK 220 made by Mitsubishi Chemical Ind. Ltd., Japan) to give 16.2 g (79.3%) of tryptophane.

EXAMPLE 16

This example illustrates the following reaction:

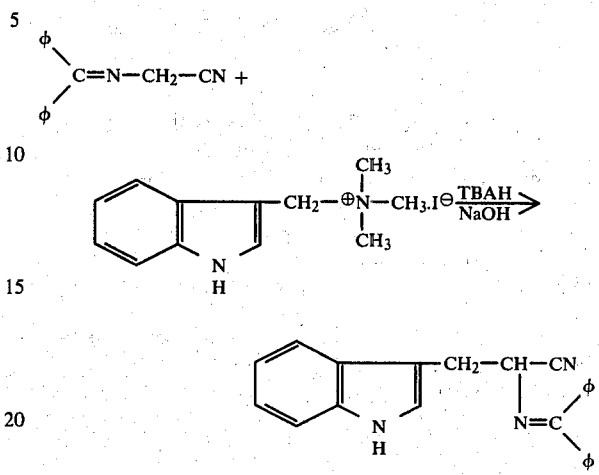

A 50 ml Erlenmeyer flask equipped with a magnetic stirring bar was charged with 2.2 g (0.01 mol) of N-(diphenylmethylene)aminoacetonitrile, 3.2 g (0.01 mol) of N,N,N-trimethyl-3-indolemethylammonium iodide, 0.7 g (2 m mol) of tetrabutylammonium hydrogensulfate (TBAH) as a phase transfer catalyst, 20 ml of dichloromethane, and 2.0 g (0.05 mol) of sodium hydroxide in 3.7 g of water (35% aqueous solution). The mixture was stirred for 3 hours at room temperature, and treated as described in Example 1 to give 2.89 g (82.7%) of 2-diphenylmethyleneamino 3-indolepropiononitrile.

EXAMPLE 17

A 50 ml Erlenmeyer flask equipped with a magnetic stirring bar was charged with 2.2 g (0.01 mol) of N-(diphenylmethylene)aminoacetonitrile, 3.0 g (0.01 mol) of N,N,N-trimethyl-3-indolemethylammonium methylsulfate, 20 ml of ethanol and 1.4 g (0.02 mol) of sodium ethylate. The mixture was stirred for 1 hour at room temperature. (Thus, the solvent consisted of a monophase system). Then, 10 ml of water were added and the ethanol was removed on a rotary evaporator with a water bath at 15°–20° C. The concentrate was extracted with chloroform and dried over anhydrous magnesium sulfate. The extract was treated as described in Example 1 to give 3.14 g (90.0%) of 2-diphenylmethyleneamino-3-indolepropionitrile.

EXAMPLE 18

This example illustrates the following reaction:

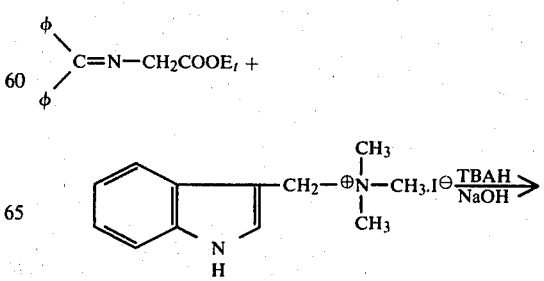

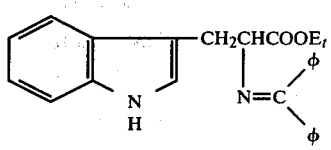

A 100 ml Erlenmeyer flask equipped with a magnetic stirring bar was charged with 5.3 g (0.020 mol) of ethyl N-(diphenylmethylene)glycinate, 6.3 g (0.020 mol) of N,N,N-trimethyl-3-indolemethylammonium iodide, 1.4 g (0.004 mol) of tetrabutylammonium hydrogensulfate as a phase transfer catalyst, 50 ml of dichloromethane, and 15 ml (0.060 mol) of 4 N aqueous sodium hydroxide solution.

The mixture was stirred for 4 hours at room temperature. Stirring was stopped. The organic phase was treated as described in Example 2 to give 6.8 g (85.5%) of ethyl 2-diphenylmethyleneamino-3-indolepropionate.

EXAMPLE 19~EXAMPLE 21

By changing only the concentration of aqueous sodium hydroxide solution, but keeping the total amount of sodium hydroxide constant, ethyl 2-diphenylmethyleneamino-3-indolepropionate was prepared in a manner similar to that in Example 18. The yields of products are shown in the Table 4.

TABLE 4

| Example No. | Concentration of Aqueous Sodium Hydroxide (N) | Yield (%) |
|---|---|---|
| 19 | 2.0 | 64.8 |
| 20 | 8.0 | 70.6 |
| 21 | 19.1 | 58.5 |

EXAMPLE 22~EXAMPLE 25

By changing only the amount of tetrabutylammonium hydrogensulfate added as a catalyst, ethyl 2-diphenylmethyleneamino-3-indolepropionate was prepared in a manner similar to that in Example 18. The yields of products are shown in Table 5.

TABLE 5

| Example No. | Amount of Tetrabutylammonium Hydrogensulfate (mol) | Yield (%) |
|---|---|---|
| 22 | 0.000 | 35.8 |
| 23 | 0.002 | 71.0 |
| 24 | 0.010 | 92.3 |

TABLE 5-continued

| Example No. | Amount of Tetrabutylammonium Hydrogensulfate (mol) | Yield (%) |
|---|---|---|
| 25 | 0.020 | 94.7 |

EXAMPLE 26

A 100 ml Erlenmeyer flask equipped with a magnetic stirring bar was charged with 2.0 g (7.5 m mol) of ethyl N-(diphenylmethylene)glycinate, 2.4 g (7.6 m mol) of N,N,N-trimethyl-3-indolemethylammonium iodide, 50 ml of dimethylformamide and 0.08 g (15 m mol) of sodium methylate. The mixture was stirred for 3 hours at room temperature. Then 10 ml of water were added and the dimethylformamide was removed under reduced pressure. The concentrate was treated as described in Example 2 to give 1.4 g (47.2%) of ethyl 2-diphenylmethyleneamino-3-indolepropionate.

EXAMPLE 27

Ethyl 2-diphenylmethyleneamino-3-indolepropionate was prepared by the reaction of ethyl N-(diphenylmethylene)glycinate with N,N,N-trimethyl-3-indolemethylammonium iodide using ethanol as the solvent instead of dimethylformamide, in a manner similar to that in Example 26. The yield of the product was 1.8 g (60.6%).

EXAMPLE 28

A 100 ml Erlenmeyer flask equipped with a magnetic stirring bar and a calcium chloride drying tube was charged with 2.0 g of ethyl N-(diphenylmethylene)glycinate, 2.4 g of N,N,N-trimethyl-3-indolemethylammonium iodide, and a suspension of 0.18 g of sodium hydride in 50 ml of dry tetrahydrofuran. The mixture was stirred for 1 hour at 0° C. Then, 10 ml of water were added and the solvent was removed under reduced pressure. The concentrate was extracted with benzene. The extract was treated as described in Example 2 to give 2.6 g (87.6%) of ethyl 2-diphenylmethyleneamino-3-indolepropionate.

EXAMPLE 29

Ethyl 2-diphenylmethyleneamino-3-indolepropionate was prepared by the reaction of ethyl N-(diphenylmethylene)glycinate with N,N,N-trimethyl-3-indolemethylammonium methylsulfate by adding 0.68 g (0.002 mol) of tetrabutylammonium hydrogensulfate in a manner similar to that in Example 2. The yield of product was 7.7 g (97.1%).

TABLE 1

| Exp. | $R^1$ | Yield (%) | MP (°C.) | Elementary Analysis calc. (found) | | | I.R. (film) (cm$^{-1}$) | $^1$H—N.M.R. (in CDCl$_3$) δ [ppm] | $^{13}$C—N.M.R. (in CDCl$_3$) δ [ppm] |
|---|---|---|---|---|---|---|---|---|---|
| | | | | C (%) | H (%) | N (%) | | | |
| 1 | CN | 89.1 | | 82.49 (82.56) | 5.48 (5.43) | 12.03 (12.01) | 3390, 3070 2935, 2250 1660, 1620 1600, 1580 1450, 1320 1280 | 3.15 (2H) 4.38 (1H) 6.5~7.7 (15H) 8.19 (1H) | 173 (1C) 54 (1C) 31 (1C) 109~138(21C) |
| 2 | COOC$_2$H$_5$ | 95.8 | 118~120 | 78.84 (78.76) | 6.17 (6.10) | 6.99 (7.07) | 3425 3060 2990 2940 1725 1620 1450 | 1.13 (3H) 3.36 (2H) 4.06 (2H) 4.31 (1H) 6.42~7.80(15H) 7.91~8.20(1H) | 172 (1C) 170 (1C) 66 (1C) 61 (1C) 29 (1C) 14 (1C) 111~139(20C) |

TABLE 1-continued

| Exp. | R¹ | Yield (%) | MP (°C.) | Elementary Analysis calc. (found) | | | I.R. (film) (cm⁻¹) | ¹H—N.M.R. (in CDCl₃) δ [ppm] | ¹³C—N.M.R. (in CDCl₃) δ [ppm] |
|---|---|---|---|---|---|---|---|---|---|
| | | | | C (%) | H (%) | N (%) | | | |
| | | | | | | | 1300~1160 (broad) | | |
| 3 | COOCH₃ | 93.7 | | 78.40 (78.51) | 5.91 (5.80) | 7.30 (7.32) | 3430 3060 2955 1740 1620 1450 1290~1170 (broad) | 3.36 (2H) 3.55 (3H) 4.40 (1H) 6.43~7.65(15H) 8.20~8.33(1H) | 173 (1C) 171 (1C) 66 (1C) 52 (1C) 29 (1C) 111~139(20C) |
| 4 | COOn-C₃H₇ | 94.2 | 110~111 | 79.16 (79.00) | 6.32 (6.38) | 6.79 (6.82) | 3400 3070 2975 1720 1620 1450 1290~1160 (broad) | 0.81 (3H) 1.48 (2H) 3.38 (2H) 4.02 (2H) 4.37 (1H) 6.30~7.75(15H) 8.10~8.24(1H) | |
| 5 | COOn-C₄H₉ | 92.5 | | 79.29 (79.22) | 6.70 (6.65) | 6.58 (6.60) | 3400 3070 2975 1730 1620 1450 1280~1180 (broad) | 0.65~1.70(7H) 3.38 (2H) 4.05 (2H) 4.39 (1H) 6.40~7.70(15H) 8.27~8.40(1H) | |

We claim:

1. A compound of Formula I,

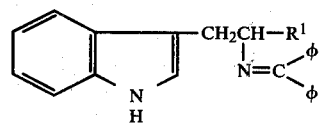

in which R¹ is selected from the group consisting of cyano, methoxycarbonyl, ethoxycarbonyl, propoxycarbonyl and butoxycarbonyl, and φ is phenyl.

2. The compound of claim 1, wherein R¹ is cyano.

* * * * *

UNITED STATES PATENT AND TRADEMARK OFFICE
CERTIFICATE OF CORRECTION

PATENT NO. : 4,399,289

DATED : August 16, 1983

INVENTOR(S) : Shinzo Imamura, Haruyo Sato and Hiroyoshi Kuramoto

It is certified that error appears in the above-identified patent and that said Letters Patent is hereby corrected as shown below:

Column 4, line 54, "1 to 6" should read --1 to 16--

Column 6, line 22, "0.0001" should read --0.001--

Column 8, line 36, before "additional" insert --an--

Column 8, line 47, "Diphenylmetheneamino" should read --Diphenylmethyleneamino--

Column 11, line 19 "(85.5%)" should read --(85.8%)--

Signed and Sealed this

Fifteenth Day of May 1984

[SEAL]

Attest:

GERALD J. MOSSINGHOFF

Attesting Officer — Commissioner of Patents and Trademarks